United States Patent [19]

Steffier

[11] Patent Number: 5,965,147

[45] Date of Patent: Oct. 12, 1999

[54] ARTIFICIAL FINGERNAILS

[75] Inventor: Larry W. Steffier, Cherry Hill, N.J.

[73] Assignee: Mycone Dental Inc., Cherry Hill, N.J.

[21] Appl. No.: 08/984,625

[22] Filed: Dec. 3, 1997

[51] Int. Cl.⁶ .................. A61K 6/00; A61K 7/00; A61K 7/04

[52] U.S. Cl. ................................. 424/401; 424/61

[58] Field of Search ................. 424/401, 61; 427/407.1

[56] References Cited

U.S. PATENT DOCUMENTS

| | | | |
|---|---|---|---|
| 2,941,535 | 6/1960 | Lappe | 132/73 |
| 3,574,822 | 4/1971 | Shepherd et al. | 424/47 |
| 3,926,892 | 12/1975 | Holcombe, Jr. | 260/29.6 |
| 3,928,113 | 12/1975 | Rosenberg | 156/344 |
| 4,058,442 | 11/1977 | Lee, Jr. et al. | 204/159.12 |
| 4,104,333 | 8/1978 | Lee, Jr. et al. | 260/885 |
| 4,209,604 | 6/1980 | Werber | 526/270 |
| 4,229,431 | 10/1980 | Lee, Jr. et al. | 424/61 |
| 4,451,629 | 5/1984 | Tanaka et al. | 526/238.23 |
| 4,626,428 | 12/1986 | Weisberg et al. | 424/61 |
| 4,669,491 | 6/1987 | Weisberg et al. | 132/73 |
| 4,712,571 | 12/1987 | Remz et al. | 132/88.7 |
| 4,766,005 | 8/1988 | Montgomery et al. | 427/4 |
| 4,863,993 | 9/1989 | Montgomery | 524/854 |
| 4,871,534 | 10/1989 | Montgomery | 424/61 |
| 5,098,696 | 3/1992 | Montgomery | 424/61 |
| 5,519,071 | 5/1996 | Rheinberger et al. | 523/116 |
| 5,523,076 | 6/1996 | Schoon | 424/61 |

OTHER PUBLICATIONS

Doug Schoon, Primer Basics Article, NAILPRO, May 1996, pp. 109, 110, 114, 115.

*Primary Examiner*—Thurman K. Page
*Assistant Examiner*—Sharon Howard
*Attorney, Agent, or Firm*—Norman E. Lehrer; Franklyn Schoenberg

[57] ABSTRACT

Materials and methods for increasing the adhesion of adhesives and coatings to proteinaceous substrates are provided wherein a liquid substantially acid-free hydrophilic acrylate monomer composition is employed to treat the substrate before application of adhesives and coating thereto.

16 Claims, No Drawings

ARTIFICIAL FINGERNAILS

FIELD OF THE INVENTION

The present invention relates to artificial fingernails and, more particularly, to materials and methods for obtaining strong adhesive bonds between coatings and adhesive compositions which are useful in such areas as artificial fingernail prosthesis in the cosmetic field and proteinaceous substrates such as human fingernails.

BACKGROUND OF THE INVENTION

The adornment, repairing and prosthetic extension of keratinaceous structures such as human fingernails and toe nails have been common practice for many years. Currently, it is known for human fingernails to be repaired with cyanoacrylate adhesives and coated with multicolored nitrocellulose and the like lacquers as well as being extended with the use of polymerizable acrylic monomer and polymer slurries or doughs. Although the nitrocellulose lacquer coatings and cyanoacrylate adhesives are generally adherent to proteinaceous substrates such as a human fingernail plate, the acrylic materials employed for the purpose of creating an artificial fingernail prosthesis and the like are not. Over the years a variety of in-situ polymerizable acrylic monomer and polymer slurry and dough compositions have been suggested for use as artificial fingernail prosthesis such as disclosed, for example, in U.S. Pat. Nos. 3,928,113; 4,048, 442; 4,104,333; 4,229,431; 4,626,428; 4,669,491; 4,766, 005; 4,871,534; 5,098,696 and 5,523,076.

Typically, only after treatment of the fingernail surface with an unsaturated carboxylic acid, such as methacrylic acid, will such polymerizable or cured acrylic compositions used for fingernail prosthesis adhere to the human fingernail plate, and even then, adhesion of the polymerized artificial fingernail materials may not persist for extended periods during normal use or until it is desired to remove the artificial fingernail. Moreover, use of such unsaturated carboxylic acids present a harsh treatment to a relatively fragile surface such as a natural human fingernail plate and poses a toxicological and dermatological hazard to living tissue of the user such as the underlying or surrounding living tissue of the fingernail plate due to the corrosive nature of these unsaturated carboxylic acids. Needless to say, "child-proof" packaging may be required for such hazardous materials. Other unsaturated carboxylic acids are also being used in the described applications including, either alone or in part, acrylic acid and beta-carboxyethyl acrylate as well as other compounds containing acid moieties. Lower concentration of these unsaturated carboxylic acids pose a decreased danger to the intact fingernail surface. However, at such lower concentrations adhesion of the polymerizable acrylic monomer and polymer slurry or dough to the fingernail plate is reduced or lost completely.

Currently, the typical known and readily practiced method for obtaining adhesion of artificial prosthetic materials to proteinaceous substrates, such as human fingernails, has been the physical abrasion and/or roughening of the proteinaceous substrate surface with a file or other abrasive material, the application of unsaturated carboxylic acid solutions as primers followed by the application and curing of the prosthetic topcoat material. These methods and materials present certain disadvantages as indicated which may be harmful to the human fingernail itself as well as to the underlying or surrounding tissue while such harsh techniques effect adhesive bonds which are frequently inadequate.

It follows from the above mentioned disadvantages that there is a need for materials and methods which are safe to use for the application of protective coatings and adhesives to proteinaceous substrates and the like and will provide improved adhesion of the coatings and adhesives such as artificial fingernail materials to proteinaceous substrates such as human fingernails. Particularly advantageous are materials and methods which effect adhesion of coating materials to the proteinaceous substrates for extended periods, preferably until it is desired by the user to remove the artificial fingernail coating, and the materials and methods reduce the preparation time and complexity of the procedure needed.

SUMMARY OF THE INVENTION

It is accordingly an object of the present invention to provide materials and methods for treating proteinaceous substrates and the like such as natural human fingernails for applying thereto a coating or adhesive such as an artificial topcoating composition suitable for forming a strong protective coating, an artificial extension or prosthesis therefore for cosmetic, protective or the like purposes which effects enhanced adhesion of the artificial topcoating to the proteinaceous substrate and is substantially not harmful to the user including the user's natural fingernail or any of the human tissue surrounding or underlying the fingernail.

It is another object of the present invention to provide materials and methods which are toxicologically and dermatologically safe for effecting enhanced adhesion between a natural human fingernail plate and an artificial topcoating composition formed by in situ polymerization of acrylic monomer and polymer compositions.

It is a further object of the present invention to provide human fingernail structures having a strong artificial protective coating or prosthesis formed of polymerized acrylic compositions which is adhered to the human fingernail surface and will perform suitably for an extended period of time or until it is desired by the user to be replaced.

These and other objects will become apparent from the description to follow.

In accordance with the present invention there is provided a pretreatment composition for increasing the adhesion of adhesives and coatings to proteinaceous substrates comprising a liquid substantially acid-free hydrophilic acrylate monomer composition.

In another aspect of the present invention there is provided a method of treating proteinaceous substrates to enhance the bonding of adhesives and coatings thereto, comprising contacting said proteinaceous substrate with a treating composition comprising a liquid substantially acid-free hydrophilic acrylate monomer composition prior to application thereto of adhesives and coatings.

In still another aspect of the present invention there is provided a method for forming human fingernail structures having an artificial fingernail protective coating or prosthesis which is strongly bonded to an underlying human fingernail substrate comprising contacting the surface of the human fingernail substrate with a treating composition comprising a liquid hydrophilic acrylate monomer composition which is substantially not harmful to the human user, preferably a solution containing at least 10 percent by weight of a substantially acid-free hydrophilic acrylate monomer, and then applying to the treated fingernail substrate a flowable composition comprising a polymerizable acrylic monomer, polymer or combinations thereof which is adapted to form a hardened protective coating or an artificial fingernail including an extension for the underlying human fingernail.

Materials and methods of the present invention have been found to be substantially harmless to the user when applied to proteinaceous substrates such as a human fingernail and to the human tissue which underlies and surrounds the fingernail while effecting enhanced adhesion of adhesives and artificial protective coatings to the substrate surface.

DESCRIPTION OF THE PREFERRED EMBODIMENTS

In accordance with the present invention materials and methods are provided which enhance the adhesive bond strength between adhesives and coatings such as artificial fingernail prosthesis to natural proteinaceous substrates such as human fingernail and toenail plates. Enhanced adhesion between the human fingernail substrate and an artificial fingernail prosthesis is readily effected using materials that are generally substantially toxicologically and dermatologically safe for the human user.

The method of this invention applies to the treatment of proteinaceous substrates and the like to be adhered to such as the surface of a human fingernail by contacting the surface of the substrate with a liquid adhesion enhancing composition comprising a liquid substantially acid-free hydrophilic acrylate monomer or preferably, a substantially acid-free solvent solution of a hydrophilic acrylate monomer or mixtures thereof. Application to the treated fingernail surface with any one of a variety of coatings or adhesive compositions, preferably a polymerizable artificial coating material suitable for forming an artificial protective coating or prosthesis including extensions for the natural fingernail, results in adhering of the adhesive or coating to the proteinaceous substrate with equal to or better bond strength than by other known methods and/or compositions such as unsaturated carboxylic acids primers for the proteinaceous substrates. Moreover, enhanced adhesion, both initially and after extended periods of time, is effected without undesirable toxicological and dermatological affects to the user including the users fingernail plate and surrounding human tissue.

In general, the method of the present invention can be accomplished by contacting a proteinaceous substrate such as a human fingernail to be adhered to with a treating composition comprising a hydrophilic acrylate monomer using a brush or other conventional method. The proteinaceous substrate may be cleaned prior to treatment with the acrylate monomer treating composition by washing, wiping with alcohol or the like, and optionally lightly roughened by use of conventional abrasive materials such as emery board.

Treating the surface to be adhered to by contacting the same with a liquid substantially acid-free hydrophilic acrylate monomer, preferably a solution comprising said polymerizable hydrophilic acrylate monomer, is an essential aspect of the present invention. A variety of liquid substantially acid-free hydrophilic acrylate monomers are suitable for use as adhesion enhancing agents. The liquid acrylate monomers may be used either at full strength or, preferably, diluted in appropriate carrier solvents. While the concentration of acrylate monomers in the treating solution is generally not critical, typically at least about 5 percent by weight, preferably at least 10 percent by weight, of polymerizable acrylate monomer should be used and most preferably at least about 25 percent by weight.

The liquid hydrophilic acrylate monomers suitable for use as adhesion enhancing agents in accordance with the present invention are substantially acid-free polymerizable liquid acrylate monomers containing at least one hydrophilic moiety such as a hydroxyl group. A variety of liquid acrylate monomers are suitable including hydroxyalkyl monoacrylates or methacrylates such as 2-hydroxymethyl acrylate, 2-hydroxyethyl methacrylate, diethylene glycol monoacrylate, diethylene glycol monomethacrylate, glycerol methacrylate, glycerol dimethacrylate, sorbitol methacrylate, dimethacrylate and trimethacrylate as well as other carbohydrate based acrylic monomers; hydroxypropyl acrylates and methacrylates, e.g. 2-hydroxypropyl acrylate, 2-hydroxypropyl methacrylate, 3-hydroxypropyl acrylate, 3-hydroxypropyl methacrylate, tetraethylene glycol monomethacrylate, pentaethylene glycol monomethacrylate, dipropylene glycol monomethacrylate and dipropylene glycol monoacrylate. Acrylamide, methacrylamide, diacetone acrylamide, methylolacrylamide and methylol methacrylamide are also useful hydrophilic monomers.

A variety of solvents and solvent mixtures are useful for preparing the adhesion enhancing agent compositions of the invention. These solvents or combination of solvents are preferably cosmetically and toxicologically acceptable and are significantly soluble in or miscible with water, although combinations of water-miscible and non water-miscible solvents may be used. Suitable solvents include but are not limited to acetone, ethyl acetate, isopropyl alcohol, ethanol, butyl acetate, n-propyl acetate, isopropyl acetate, cyclohexane, n-hexane, isobutyl acetate, amyl acetate, isoamyl acetate, butanol, acetonitrile and mixtures thereof. In formulating the adhesion enhancing agents of the invention, attention should be paid to the use of solvents that are not harmful to human tissue or pose a significant environmental hazard, and are sufficiently volatile to evaporate completely in a reasonable amount of time. In general, preferred solvent include ethyl acetate, isopropanol, ethanol and mixtures thereof.

Additional materials conventionally used in fingernail coating compositions may be present in the adhesion enhancing compositions of the invention provided such materials do not adversely affect the properties thereof as an adhesion enhancing agent. Optionally, the compositions of the invention may include a polymerization catalyst or accelerators for polymerizable acrylate monomers such as benzoyl peroxide or dimethyl paratoluidine as well as up to about 30 percent by weight of polymeric acrylates including hydrophilic polymers and copolymers such as poly, copoly or terpolymers of hydroxyalkyl methacrylate containing hydrophilic moieties.

As indicated, the method of the invention comprises treatment of proteinaceous substrates and the like to be adhered to by contacting the surface thereof with a liquid substantially acid-free hydrophilic acrylate monomer, preferably a solution of the hydrophilic acrylate monomer, and then applying to the treated surface any of a variety of adhesive or coating compositions which, after polymerization, will achieve the desired result such as protective fingernail coating, fingernail extension or prosthesis. The adhesive or coating will adhere to the proteinaceous substrate with equal or better bond strengths than effected by the use of other harsher and/or potentially harmful methods and compositions. The amount of adhesive enhancing treating composition that may be applied to the substrate is not critical and generally a single application would be suitable, but the amount most advantageously used may vary depending on the condition of the proteinaceous surface to be treated such as the porosity thereof, as well as differences that typically exist between different human fingernail plates. Moreover, while the treating composition may be allowed to dry by evaporation of the solvent components before the adhesive or coating composition may be applied to the treated surface, it is generally preferred to apply the adhesive or coating composition to the substrate before the treating composition has dried.

The adhesive and coating compositions to which the present invention applies for improving the adhesion strength thereof to proteinaceous substrates can be taken to mean any of a variety of known acrylate polymeric or monomer compositions that can be stored in either single or multi-component form, is used to adhere, cover, adorn, replace or otherwise protect a proteinaceous substrate such as a human fingernail plate and can be polymerized by one or more of a variety of free radical-type initiation processes. Examples of such materials are:

1) two-component (powder and liquid) artificial fingernail prosthesis formulations which polymerize through a peroxide/tertiary amine type initiation;
2) ultraviolet and visible light as well as heat cured, unfilled, or filled, coatings and adhesives used to attach and/or cover natural or artificial fingernails; and
3) Cyanoacrylate adhesive formulations The following examples are given for the purpose of illustration and are not intended in any way to limit the invention as claimed. Unless noted to the contrary, proportions are on a weight basis.

EXAMPLE 1

The adhesion enhancing characteristics of the liquid hydrophilic acrylate monomer treating compositions of this invention are compared to other known adhesion promoters in connection with the adhesion of an artificial fingernail composition useful in the artificial fingernail art.

To illustrate the extent of adhesion enhancement by the method and materials of this invention, experienced operators are chosen to apply artificial fingernail extensions to the natural fingernail plates of human subjects. Adhesion of an artificial fingernail extension to the subject is observed 3 days, 7 days and 14 days after application of the artificial nails and lifting of the artificial nail (adhesion failure) from the human fingernail is noted. A variety of liquid hydrophilic acrylate monomer treating compositions to be evaluated are listed below.

| | Treating Compositions | |
|---|---|---|
| A. | Hydroxyethyl methacrylate (HEMA) | 100% |
| B. | Hydroxyethyl methacrylate | 75% |
| | Isobutyl acetate | 25% |
| C. | Hydroxyethyl methacrylate | 75% |
| | Ethyl acetate | 25% |
| D. | Hydroxyethyl methacrylate | 40% |
| | Ethyl acetate | 60% |
| E. | Hydroxyethyl methacrylate | 40% |
| | Isobutyl acetate | 60% |
| F. | Hydroxyethyl methacrylate | 50% |
| | Trimethlolpropane Trimethacrylate | 0.5% |
| | Cellulose acetate propionate | 10% |
| | Ethyl acetate | 39.5% |
| G. | Hydroxyethyl methacrylate | 19.9% |
| | Isobutyl methacrylate | 3.3% |
| | Ethyl acetate | 45.8% |
| | N butyl acetate | 31.0% |
| H. | Sorbitol dimethacrylate | 50% |
| | Ethyl Acetate | 25% |
| | Ethanol | 25% |
| I | Glycerol methacrylate | 50% |
| | Ethyl acetate | 50% |

| | -continued | |
|---|---|---|
| | Treating Compositions | |
| J. | Glycerol methacrylate | 50% |
| | Ethyl acetate | 25% |
| | Ethanol | 25% |
| K. | Sorbitol methacrylate | 25% |
| | Ethanol | 25% |
| | Isobutyl acetate | 50% |
| L | Sorbitol methacrylate | 10% |
| | Water | 45% |
| | Ethanol | 45% |

The artificial fingernail composition used has the following proportion of ingredients.

| | |
|---|---|
| Polymeric Powder | |
| Poly(ethyl methacrylate) | 98.4% |
| Benzoyl peroxide | 1.6% |
| Liquid Binder | |
| Ethyl methacrylate | 90.0% |
| Ethylene glycol dimethacrylate | 8.7% |
| Dimethyl-p-toluidine | 1.2% |
| MEHQ | (25 ppm) |
| Benzophenone | (500 ppm) |

The above components when combined in a ratio of about one part of liquid binder to about two parts of polymeric powder immediately prior to application to the substrate surface result in a suitable workable dough for forming an artificial fingernail.

The adhesion enhancing capabilities of the above treating compositions are compared with methacrylic acid (MAA) and solutions containing methacrylic acid (MAA). The results determined after 3 days, 7 days and 14 days are reported in Table I below:

TABLE I

| | % Lifting (average) | | |
|---|---|---|---|
| Treating Composition | 3 days | 7 days | 14 days |
| None | >30 | >50 | — |
| 99.8% MAA | 5 | 10 | 15 |
| 90% MAA | 10 | 10 | 20 |
| 50% MAA | 20 | 40 | — |
| A (100% HEMA) | 5 | 20 | 25 |
| B (75% HEMA) | 0 | 5 | 10 |
| C (75% HEMA) | 0 | 0 | 0 |
| D (40% HEMA) | 0 | 0 | 10 |
| E (40% HEMA) | 0 | 0 | 5 |
| F (50% HEMA) | 0 | 0 | 10 |
| G (19.9% HEMA) | 0 | 0 | 0 |
| H | 0 | 0 | 0 |
| I | 0 | 0 | 0 |
| J | 0 | 0 | 0 |
| K | 0 | 0 | 0 |
| L | 10 | 20 | 20 |

It is evident from the results reported above that the treatment compositions A–L enhanced the adhesion of an artificial fingernail composition to a human fingernail plate as compared to no adhesion primers being used, and that the enhanced adhesion was comparable to or superior to the use of known prior art primers.(MAA)

EXAMPLE 2

Experienced operators are chosen to apply artificial fingernail extensions to the natural fingernail plates of 12 human subjects. Treating Composition G of example 1 is used to treat the nail plates of human subjects prior to using the artificial fingernail composition described in example 1. For comparison, a similar number of operators are used to apply artificial fingernail extensions wherein a primer of methacrylic acid is used on the fingernail plate prior to application of the artificial fingernail extension material. The test results obtained after 3, 7 and 14 days show that adhesion failures with both sets of nail plate treatments is less than 5.7% for all the human subjects and the adhesion failures using Composition G were somewhat lower after 3, 7 and 14 days.

EXAMPLE 3

In this example, tests are performed with an artificial fingernail composition containing 60 micron polyethylmethacrylate nail polymer with 0.8% benzoyl peroxide added and a liquid nail monomer containing 80% ethyl methacrylate, 10% HEMA, 9% triethylene glycol dimethacrylate, 0.9% N, N-Dimethyl para toluidine, 30 ppm MEHQ and 30 ppm benzophenone. Two coatings of fingernail treating compositions described below are applied to the fingernail plate before the artificial fingernail compositions are applied to the fingernail plates.

|  |  | LIFTING (%) | | |
|---|---|---|---|---|
|  |  | Day 3 | Day 7 | Day 14 |
| Treating Composition 1 |  | 10 | 20 | 20 |
| glycerol dimethacrylate | 5% | | | |
| ethyl acetate | 40% | | | |
| ethanol | 55% | | | |
| Treating Composition 2 |  | 0 | 0 | 10 |
| glycerol methacrylate | 25% | | | |
| H2O | 25% | | | |
| ethanol | 50% | | | |
| Treating Composition 3 |  | 10 | 30 | 30 |
| sorbitol methacrylate | 25% | | | |
| H2O | 75% | | | |
| Primer |  | | | |
| methacrylic acid | 100% | 10 | 10 | 20 |
| No Primer Used |  | 40 | — | — |

It is evident from the above results that the adhesion enhancing treatment compositions of the present invention are substantially comparable to the use of methacrylic acid primer and both are superior to results obtained without a primer.

EXAMPLE 4

The same nail polymer (polyethylmethacrylate) as employed in example 3 is used in this example. The liquid nail monomer composition of example 3 is also used except 10% cellulose acetate butyrate is added increasing the viscosity of the monomer. Artificial fingernail coatings on human fingernail plates are prepared as follows: primer is applied twice, the viscous monomer is applied to the treated nail plate, then the nail polymer is sprinkled on the wet monomer and polymer is brushed off. Additional monomer is applied as well as polymer and then brushed off. After 10 minutes the nail treatment coating is filed and coated with nail lacquer.

The nail treating compositions used in this example are described below together with the results obtained for the various artificial fingernail preparations.

|  |  | LIFTING (%) | | |
|---|---|---|---|---|
|  |  | Day 3 | Day 7 | Day 14 |
| Treating Composition 1 |  | 20 | 20 | 20 |
| gylcerol dimethacrylate | 5% | | | |
| ethyl acetate | 40% | | | |
| ethanol | 55% | | | |
| Treating Composition 2 |  | 10 | 10 | 20 |
| glycerol methacrylate | 25% | | | |
| H2O | 25% | | | |
| ethanol | 50% | | | |
| Treating Composition 3 |  | 20 | 30 | 40 |
| sorbitol methacrylate | 25% | | | |
| H2O | 75% | | | |
| Primer 4 |  | | | |
| methacrylic acid | 100% | 10 | 10 | 20 |
| No Primer Used |  | 80 | — | — |

EXAMPLE 5

In this example a primer is applied to the natural fingernail plates of a group of human subjects and then alkyl cyano acrylate glue is applied to the treated fingernail plate in place of a liquid monomer component. Polymethylmethacrylate homopolymer is sprinkled on top of the glue and allowed to dry for 10 minutes before further working. The treating compositions used and results obtained are reported below.

|  |  | LIFTING (%) | | |
|---|---|---|---|---|
|  |  | Day 3 | Day 7 | Day 14 |
| Treating Composition 1 |  | 0 | 0 | 10 |
| gylcerol dimethacrylate | 5% | | | |
| ethyl acetate | 40% | | | |
| ethanol | 55% | | | |
| Treating Composition 2 |  | 0 | 10 | 10 |
| gylcerol methacrylate | 25% | | | |
| H2O | 25% | | | |
| ethanol | 50% | | | |
| Treating Composition 3 |  | 0 | 0 | 0 |
| sorbitol methacrylate | 25% | | | |
| H2O | 75% | | | |
| Primer |  | 0 | 10 | 20 |
| methacrylic acid | 100% | | | |
| No Primer Used |  | 10 | 20 | 20 |

EXAMPLE 6

In this example the use of urethane acrylate oligomer gel chemistry in place of both artificial monomer and polymer topcoat mixtures is illustrated. The artificial fingernails are prepared using a standard aliphatic solvent mixture; used to clean the nail plate. The fingernail Treating Compositions are applied to the natural fingernail plate twice, a UV reactive/curable acrylate oligomer manufactured by KUPA INC. designated "One Phase Gel" Item #502 is applied to the treated fingernail and then cured under a 9 watt UV lamp. The Treating Compositions applied to the fingernail plate and the results are as follows:

|  |  | LIFTING (%) | | | |
|---|---|---|---|---|---|
|  |  | Day 3 | Day 7 | Day 14 | Day 21 |
| Treating Compositions 1 |  | 0 | 0 | 0 | 0 |
| glycerol dimethacrylate | 5% | | | | |

-continued

| | | LIFTING (%) | | | |
|---|---|---|---|---|---|
| | | Day 3 | Day 7 | Day 14 | Day 21 |
| ethyl acetate | 40% | | | | |
| ethanol | 55% | | | | |
| Treating Composition 2 | | 0 | 10 | 10 | 10 |
| glycerol methacrylate | 25% | | | | |
| H2O | 25% | | | | |
| ethanol | 50% | | | | |
| Treating Composition 3 | | 0 | 0 | 0 | 10 |
| sorbitol methacrylate | 25% | | | | |
| H2O | 75% | | | | |
| Primer | | 0 | 0 | 10 | 10 |
| methacrylic acid | 100% | | | | |
| No primer Used | | 30 | 50 | — | — |

It will be evident from the above that there are other embodiments of the compositions and methods, which while not expressly described above, are clearly, within the scope and spirit of the invention. The description above, is therefore intended to be exemplary only and the scope of this invention is to be limited solely by the appended claims.

What is claimed is:

1. A pretreatment composition for increasing the adhesion of adhesives and coatings to proteinaceous substrates comprising a liquid substantially acid-free hydrophilic acrylate monomer composition.

2. The pretreatment composition as claimed in claim 1, wherein said composition contains at least about 5 percent by weight of said liquid hydrophilic acrylate monomer composition and further comprises a solvent.

3. The pretreatment composition as claimed in claim 1, wherein said liquid hydrophilic acrylate monomer composition is a polymerizable liquid acrylate monomer containing at least one hydrophilic moiety.

4. The pretreatment composition as claimed in claim 1, wherein said liquid hydrophilic acrylate monomer composition is selected from the group consisting of hydroxyalkyl monoacrylates or methacrylates, carbohydrate based acrylic monomers, alkylacrylamide and mixtures of the same.

5. The pretreatment composition as claimed in claim 1, wherein said liquid hydrophilic acrylate monomer composition is selected from the group consisting of hydroxyalkyl monoacrylates or methacrylates, carbohydrate based acrylic monomers and mixtures of the same.

6. A method of treating proteinaceous substrates to enhance the bonding of adhesives and coatings thereto comprising contacting the proteinaceous substrate with a treating composition comprising a liquid substantially acid-free hydrophilic acrylate monomer composition prior to application thereto of adhesives and coatings.

7. The method of treating proteinaceous substrates as claimed in claim 6, wherein said treating composition comprises a composition containing at least about 5 percent by weight of said liquid hydrophilic monomer.

8. The method of treating proteinaceous substrates as claimed in claim 6, wherein said liquid substantially acid-free hydrophilic monomer composition is selected from the group consisting of 2-hydroxymethyl acrylate, 2-hydroxyethyl methacrylate, diethylene glycol monoacrylate, diethylene glycol monomethacrylate, glycerol methacrylate, glyercol dimethacrylate, sorbitol methacrylate, dimethacrylate and trimethacrylate, 2-hydroxypropyl acrylate, 2-hydroxypropyl methacrylate, 3-hydroxypropyl acrylate, 3-hydroxypropyl, methacrylate, tetraethylene glycol monomethacrylate, pentaethylene glycol monomethacrylate, dipropylene glycol monomethacrylate, dipropylene glycol monoacrylate, and alkylacrylamide.

9. A method of forming human fingernail structures having an artificial nail surface attached thereto comprising contacting a human fingernail substrate with a treating composition comprising a liquid substantially acid-free hydrophilic acrylate monomer composition; applying to the treated fingernail substrate a flowable composition comprising a polymerizable acrylic monomer, polymer or combinations thereof which is adaptable to form a hardened cross-linked polymer protective coating therefore; and allowing said flowable composition to polymerize and harden to form an artificial nail surface for said underlying human fingernail substrates.

10. The pretreatment composition as claimed in claim 1, wherein said pretreatment composition consists essentially of a liquid substantially acid-free polymerizable hydrophilic acrylate monomer, a liquid substantially acid-free polymerizable hydrophobic methacrylate monomer and mixtures thereof and wherein application of said pretreatment composition to a proteinaceous substrate prior to the application thereto of adhesive and coatings enhances adhesion of said adhesives and coatings thereto.

11. The pretreatment composition as claimed in claim 1, wherein said treatment composition contains at least about 25 percent by weight of said hydrophylic acrylate monomer composition and further contains a cosmetically and toxicologically acceptable solvent or combination of solvents.

12. The pretreatment composition as claimed in claim 11, wherein said solvent is water soluble, miscible in water or a combination thereof.

13. The method of treating proteinaceous substrates as claimed in claim 6, wherein said treating composition consists essentially of a liquid substantially acid-free hydrophilic monomer composition and mixtures of the same and wherein treating a proteinaceous surface prior to the application thereto of adhesives and coatings substantially enhances adhesion of the adhesives and coatings thereto.

14. The method of treating proteinaceous substrates as claimed in claim 13, wherein said proteinaceous substrate is a human fingernail.

15. The method of treating proteinaceous substrates as claimed in claim 14, wherein said treatment composition contains at least about 25 percent by weight of said hydrophylic acrylate monomer composition and further contains a cosmetically and toxicologically acceptable solvent or combination of solvents.

16. The method of treating proteinaceous substrates as claimed in claim 14, wherein said adhesives and coatings are polymerizable artificial coating materials adaptable for forming an artificial coating, prosthesis and/or extension for said human fingernail.

* * * * *